United States Patent [19]

Wunsch

[11] Patent Number: 4,599,407

[45] Date of Patent: Jul. 8, 1986

[54] THIOHYDRAZINE-1,2-DICARBOXYLIC ACID DERIVATIVES AND PROCESS FOR THEIR PREPARATION

[75] Inventor: Erich Wunsch, Tutzing, Fed. Rep. of Germany

[73] Assignee: Max Planck Gesellschaft zur Forderung der Wissenschaften e.V., Fed. Rep. of Germany

[21] Appl. No.: 762,819

[22] Filed: Aug. 5, 1985

Related U.S. Application Data

[63] Continuation of Ser. No. 538,350, Oct. 3, 1983, abandoned.

[30] Foreign Application Priority Data

Oct. 5, 1982 [DE] Fed. Rep. of Germany ....... 3236849

[51] Int. Cl.⁴ .................. C07C 161/00; C07D 265/28
[52] U.S. Cl. ..................... 544/85; 560/312; 530/336; 560/137; 560/148
[58] Field of Search ............... 260/453 RW; 560/137, 560/148; 544/85

[56] References Cited

PUBLICATIONS

Yoneda et al., J. Org. Chem., vol. 32 (1967), pp. 727–729.
Mukaiyama et al., Tet. Letters, No. 56, (1968), pp. 5907–5908.

*Primary Examiner*—Richard L. Raymond
*Attorney, Agent, or Firm*—Robbins & Laramie

[57] ABSTRACT

The invention concerns new 1-tert.-alkyl-thiohydrazine-1,2-dicarboxylic acid derivatives, their production, and their use as reagents for the transfer of a 1-tert.-alkylthio residue, particularly of a 1-tert.-butylthio residue as a protective group for thiols.

7 Claims, No Drawings

THIOHYDRAZINE-1,2-DICARBOXYLIC ACID DERIVATIVES AND PROCESS FOR THEIR PREPARATION

This application is a continuation of application Ser. No. 538,350, filed Oct. 3, 1983, now abandoned.

Several processes are known for reversibly masking mercapto groups of cysteine. Thus, the cysteine can be converted into the S-benzyl derviative, but conditions must be used for cleavage that may result in undesirable secondary reactions. Masking of the SH group as an S-diphenylmethyl or S-trityl derivative, on the other hand, severely restricts the use of numerous other protective groups due to the easy cleavability of these thioethers. In addition, the use of S-ethyl mercaptocysteine, i.e. an unsymmetrical disulfide with a cysteine residue (*Bull. Chem. Soc. Japan* 40, 2913 (1967)) for peptide syntheses does not inhibit the known disproportionation of unsymmetrical disulfides into symmetrical ones. Oxidation of the disulfide bond can occur here as well, with formation of sulfinic acid thioesters.

The applicant therefore developed some time ago (DE-PS No. 19 23 480) a process in which the mercapto group of the cysteines is protected by introducing the tert.-butylmercapto group. In this process the protective group is introduced by cleaving the disulfide bridge of cystine through the addition of an excess of tert.-butylmercaptan. At room temperature this reaction requires at least several days and up to about a week. Although this protective group has proven itself very well, the previously known methods for its introduction are problematic, on the one hand due to the duration of the named reaction and on the other hand due to the excess amount of mercaptan that must be applied, which, particularly on a large scale, represents a considerable environmental problem due to the noxious odor resulting from preparation of the excess.

The object of the invention is, therefore, to prepare new agents and methods for introducing the tert.-butylmercapto protective group or similarly bulky tert.-alkylthio protective groups in thiols, particularly in cysteine, cysteine derivatives, and cysteine peptides.

It has been discovered that 1-tert.-alkylthiohydrazine-1,2-dicarboxylic acid derivatives of the general formula

in which
R$^1$ is a tertiary alkyl group, specifically, tert.-butyl or tert.-amyl and
R$^2$ is an ester or amide residue are easily prepared and represent an excellent reagent for the introduction of tert.-alkylthio protective groups, particularly the tert.-butyl- and tert.-amylthio groups.

It is well known (Teruaki Mukaiyama and Katsuji Takahashi, *Tetrahedron Letters* 56, 5907–5908, (1968)) to react diethylazodicarboxylate with n-ethyl and n-amyl mercaptan to produce unsymmetrical disulfides, according to the following reaction scheme and under mild, neutral conditions,

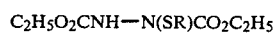

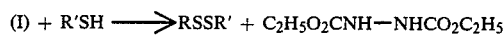

However, this known reaction will not occur with sterically hindered alkylmercaptans, e.g. tert.-butylmercaptan.

Now, however, it has been discovered that a quantitative reaction can also be achieved with tert.-butylmercaptan if catalytic amounts of a very strong base are added to the reaction medium, whereby 1-tert.-alkylthiohydrazine-1,2-dicarboxylic acid derivatives are obtained, which represent an excellent reagent for transferring the 1-tert.-alkylthio group.

In the 1-tert.-alkylthiohydrazine-1,2-dicarboxylic acid derivatives of the general formula I in accordance with the invention, the substituent R$^1$ represents a tertiary alkyl group suitable for the invention objective, in particular, the tert.-butyl group, although the tert.-amyl group can also be used.

The substituent R$^2$ represents a suitable ester or amide residue. Suitable ester residues can be derived from alkyl alcohols, for example those with 1-6 C-atoms, particularly 1-4 C-atoms, such as methyl-, ethyl-, propyl-, n-butyl-, tert.-butyl alcohol or can be derived from aryl alcohols, such as phenol, or from aralkyl alcohols.

Suitable amide residues are derived from ammonia, mono- or dialkyl amines, mono- or diaryl amines, or cyclical amines, such as morpholine. The preferred alkyl amines have 1-6 C-atoms and phenyl is the preferred aryl. The solubility properties of the reagents in accordance with the invention, which are dependent on the selected reaction medium, can be influenced through suitable selection of the ester and amide residues. It was found that dimorpholide is particularly suitable for transferring the tert.-butylthio group in an aqueous medium, as well as in an aqueous organic medium such as dioxane/water, acetonitrile/ammonium acetate buffer, or two phase ethyl acetate/water.

The di-tert.-butyl ester is especially preferred among the ester derivatives which are easily soluble in organic solvents.

The reagents in accordance with the invention can be prepared by reacting a tert.-alkylmercaptan of the general formula II

in which R$^1$ has the meaning indicated above, with an azodicarboxylic acid derivative of the general formula III

in which R² has the meaning indicated above, in an inert, aprotic solvent, in the presence of a catalytic amount of a very strong base.

Suitable inert aprotic solvents are diethylether, dioxane, or tetrahydrofuran. Numerous other suitable solvents are known to the specialist.

Strong bases, whose presence is required in a catalytic amount, are alkali metal or alkaline earth metal alcoholates, amides, hydrides, or hydroxides. Sodium or potassium methylate or ethylate, sodium or potassium amide, sodium or potassium hydride, and sodium or potassium hydroxide may be named as examples.

The reaction is effectively performed at a temperature between room temperature and the boiling temperature of the solvent. It proceeds exothermically.

The reagents in accordance with the invention can be isolated through crystallization and recrystallization after removal of the solvent. They are highly stable during storage.

The reagents in accordance with the invention are very well-suited for transferring the tert.-butylthio residue to thiols, e.g. cysteine and cysteine derivatives and peptides. By means of this method, the availability of S-tert.-butylthiocysteine is possible for the first time in high yields in a process that is very compatible with the environment (no odor pollution). S-tert.-butylthiocysteine was subsequently recognized as an extremely favorable cysteine derivative for the synthesis of cysteine and cystine peptides (Moroder, L., Gemeiner, M., Gohring, W., Jaeger, E., Thamm, P., and Wunsch, E., *Biopolymers* 20, 17-37 (1981)).

In addition, the 1-tert.-butylthiohydrazine-1,2-dicarboxylic acid derivatives in accordance with the invention make possible a reversible labelling of the cysteine-thio functions in peptides and proteins, as is necessary:

(1) in amino acid sequence analysis;

(2) in chemical or enzymatic semisynthesis;

(3) in the synthesis of cystine- or cysteine peptides through additional, intermediate protection of the cysteine-thiol function;

(4) in the specific-purpose synthesis of asymmetrical cystine peptides for trapping the excess cysteine components, whereby the obtained, isolatable S-protected cysteine components can be reused after the cleavage of the S-protective group (recycling process).

The specific-purpose synthesis of asymmetrical cystine peptides by means of the sulfenohydrazide method is described in the literature (Wunsch, E., and Romani, S., *Hoppe-Seyler's Z. Physiol. Chem.* 363, 449-453 (1982); Romani, S., Gohring, W., Moroder, L. and Wunsch, E., *Proceedings of the 4th FRG-USSR Symposium on Chemistry of Peptides and Proteins, Tubingen,* (June 8-12, 1982); Wunsch, E., Romani, S., and Moroder, L., in *Proceedings of the 17th European Peptide Symposium,* Prague, (Aug. 29-Sept. 3, 1982)). The invention thus encompasses processes which employ the reagents in accordance with the invention.

In order to suppress the time-dependent, thiol-induced disproportionation of the asymmetric cystine peptide to the symmetric disulfides in asymmetric cystine peptide synthesis, it is recommended that either a large excess of the activated sulfenohydrazide components be employed, or the unreacted thiol components be trapped out of the reaction mixture as soon as the maximum concentration of asymmetric cystine peptides is achieved.

However, the maleimide derivatives previously used as thiol reagents form irreversible conjugates with the SH components, which represents a not inconsiderable loss, particularly in the case of larger peptides. However, if the reagents in accordance with the invention are used to block the excess thiol components, the tert.-butylthio-protected cysteine peptide can be almost quantitatively recovered.

EXAMPLE 1

Preparation of 1-tert.-butylthiohydrazine-1,2-dicarboxylic acid dimorpholide (a) Azodicarboxylic acid dimorpholide 17.4 g. (0.2M)morpholine in 100 ml. ether are dripped into a solution of 17.4 g (0.1M) azodicarboxylic acid diethyl ester in 100 ml. ether. The resulting, orange-colored precipitate is stirred for 5 hours at room temperature and filtered out. A further fraction is obtained from the filtrate after concentration in a vacuum and addition to a small amount of petroleum ether.

Yield 18.6 g. (73% of theoretical) Melting point 141°-143° C.

$C_{10}H_{14}N_4O_4$ (256.265)—Theoretical: C 46.87, H 6.29, N 21.86. Actual: C 46.49, H 6.30, N 21.67.

(b) 1-tert.-butylthiohydrazine-1,2-dicarboxylic acid dimorpholide

Catalytic amounts of sodium methylate are added to a solution of 2.3 ml (0.02M) tert.-butylmercaptan and 5.12 g. (0.02M) azodicarboxylic acid dimorpholide in 150 ml. tetrahydrofuran. The reaction proceeds exothermically. The reaction mixture is concentrated by one half in a vacuum and the sulfenohydrazide (1-tert.-butylthiohydrazine-1,2-dicarboxylic acid dimorpholide) crystallizes out after the addition of petroleum ether.

Yield 6.44 g. (93% of theoretical) Melting point 152°-154° C.

$C_{14}H_{26}N_4O_4 S$ (346.448)—Theoretical: C 48.54, H 7.56, N 16.17, S 9.25. Actual: C 48.11, H 7.42, N 16.31, S 9.28.

EXAMPLE 2

Preparation of 1tert.-butylthiohydrazine-1,2-dicarboxylic acid di-tert.-butyl ester A catalytic amount of sodium ethylate is added to a solution of 1.15 g. (0.005M) azodicarboxylic acid di-tert.-butyl ester and 0.57 ml. (0.005M) tert.-butylmercaptan in 20 ml. ether. The reaction proceeds exothermically. The solvent is removed in a vacuum and the oil residue is recrystallized from n-hexane.

Yield 1.54 g. (96% of theoretical) Melting point 92°-96° C.

$C_{14}H_{28}N_2O_4S$ (320.45)—Theoretical: C 52.47, H 8.81, N 8.74, S 10.00. Actual: C 52.45, H 8.80, N 8.78, S 9.93.

EXAMPLE 3

Preparation of S-tert.-butylthio-cysteine

A solution of 0.6 g. (0.005M) cysteine in 20 ml. argon-saturated water is slowly dripped into a suspension of 3.4 g. (0.01M) 1-tert.-butylthiohydrazine-1,2-carboxylic acid dimorpholide in 40 ml. argon-saturated water. A clear solution results, from which the S-tert.-butylthiocysteine begins to precipitate after one hour. After 12 hours, the precipitate is filtered off and the excess reagent is extracted from the filtrate with ethyl acetate. The aqueous phase is concentrated in a vacuum and a further fraction is crystallized out upon standing in the cold.

Yield 84% (of theoretical) Decomposes at 176° C.

$[\alpha]_D^{20°} -89.6°$ or $[\alpha]_{546}^{20°} = -106.7°$ (c=1 in 1N HCl).

$C_7H_{15}NO_2S_2 \cdot \frac{1}{2}H_2O$ (218.344)—Theoretical: C 38.51, H 7.39, N 6.42, S 29.37. Actual: C 38.35, H 7.36, N 6.83, S 29.17.

EXAMPLE 4

Preparation of N-tert.-butyloxycarbonyl-O-tert.-butyl-L-threonyl-L-alanyl-S-(tert.-butylthio)-L-cysteinyl-glycyl-L-glutaminyl-N$^\epsilon$-tert.-butyloxycarbonyl-L-lysyl-O-tert.-butyl-L-seryl-L-proline-tert.-butyl ester.

A solution of 302 mg. (0.26 mM) Boc-Thr(t-Bu)-Ala-Cys-Gly-Gln-Lys(Boc)-Ser(t-Bu)-Pro-O-t-Bu in 10 ml. argon saturated dimethylformamide is dripped into a solution of 250 mg. (0.78 mM) 1-tert.-butylthiohydrazine-1,2-dicarboxylic acid di-tert.-butyl ester in 5 ml. argon-saturated dimethylformamide under an argon atmosphere. After 12 hours of stirring at room temperature, the reaction solution is concentrated in a vacuum and added to petroleum ether. The precipitate is filtered off and recrystallized from methanol/petroleum ether.

Yield 300 mg. (93% of theoretical) Melting point 192°–194° C.

$[\alpha]_D^{20°} = -56.8°$ or $[\alpha]_{546}^{20°} = -67.5°$ (c=1 in ethanol).

$C_{57}H_{102}N_{10}O_{16}S_2 \cdot H_2O$ (1265.66)—Theoretical: C 54.09, H 8.29, N 11.07, S 5.06. Actual: C 54.17, H 8.34, N10.69, S 4.82.

What is claimed is:

1. A 1-tert.-alkyl-thiohydrazine-1,2-dicarboxylic acid derivative of the general formula I $$R^1-S-N-CO-R^2 \atop H-N-CO-R^2 \qquad (I)$$

in which
R$^1$ is a tertiary butyl or a tertiary amyl group, and
R$^2$ is an ester or amide residue.

2. 1-tert.-butylthiohydrazine-1,2-dicarboxylic acid dimorpholide.

3. 1-tert.-butylthiohydrazine-1,2-dicarboxylic acid di-tert.-butyl ester.

4. A process for the preparation of a compound of the general formula $$R^1-S-N-CO-R^2 \atop N-CO-R^2$$

in which R$^1$ is a tertiary alkyl group and R$^2$ is an ester or amide residue, wherein a tert.-alkylmercaptan of the general formula II $$R^1-S-H \qquad (II)$$

in which R$^1$ is as previously defined, is reacted with an azodicarboxylic acid derivative of the general formula III $$R^2-OC-N=N-CO-R^2 \qquad (III)$$

in which R$^2$ is as previously defined, in an inert, aprotic solvent in the presence of a catalytic amount of a very strong base.

5. The process of claim 4 wherein the very strong base is an alkali metal or alkaline earth metal alcoholate, amide, hydride, or hydroxide.

6. The process of claim 4 wherein R$^1$ is tert.-butyl or tert.-amyl.

7. The process of claim 6 wherein the very strong base is an alkali metal or alkaline earth metal alcoholate, amide, hydride, or hydroxide.

* * * * *